(12) United States Patent
Wang

(10) Patent No.: US 9,314,500 B2
(45) Date of Patent: Apr. 19, 2016

(54) NON-N-GLYCOSYLATED RECOMBINANT HUMAN ANNEXIN A2

(71) Applicant: The General Hospital Corporation, Boston, MA (US)

(72) Inventor: Zhirui Wang, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/351,008

(22) PCT Filed: Oct. 11, 2012

(86) PCT No.: PCT/US2012/059772
§ 371 (c)(1),
(2) Date: Apr. 10, 2014

(87) PCT Pub. No.: WO2013/055929
PCT Pub. Date: Apr. 18, 2013

(65) Prior Publication Data
US 2015/0105322 A1    Apr. 16, 2015

Related U.S. Application Data

(60) Provisional application No. 61/546,196, filed on Oct. 12, 2011.

(51) Int. Cl.
| | |
|---|---|
| *C12N 15/81* | (2006.01) |
| *C07K 1/00* | (2006.01) |
| *A61P 9/10* | (2006.01) |
| *C12N 15/12* | (2006.01) |
| *C12N 5/10* | (2006.01) |
| *A61K 38/17* | (2006.01) |
| *C07K 14/47* | (2006.01) |
| *A61K 38/00* | (2006.01) |

(52) U.S. Cl.
CPC ............. *A61K 38/1709* (2013.01); *C07K 14/47* (2013.01); *C07K 14/4721* (2013.01); *A61K 38/00* (2013.01); *C07K 2319/21* (2013.01)

(58) Field of Classification Search
None
See application file for complete search history.

(56) References Cited

U.S. PATENT DOCUMENTS

| 2002/0128444 A1* | 9/2002 | Gingras et al. ................ 530/350 |
| 2011/0118181 A1 | 5/2011 | Seidah et al. |
| 2011/0129526 A1 | 6/2011 | Wang et al. |
| 2011/0201052 A1 | 8/2011 | Raitano et al. |

OTHER PUBLICATIONS

Ishii et al. (Circ Res (20010 89: 1240-1245).*
Thermo Scientific, Pierce Protein Biology Products "Peptide Design" (2014, downloaded from https://www.lifetechnologies. com/us/en/home/life-science/protein-biology/protein-biology-learning-center/protein-biology-resource-library/pierce-protein-methods/peptide-design.html.*
Okabayashi et al (Gene (Oct. 24, 1996) 177(1-2): 69-76).*
Cregg, Methods Mol. Biol. 389 (2007) 1-10.*
Brondyk, Methods Enzymol. 463 (2009) 131-147.*
International Preliminary Report on Patentability in International Application No. PCT/US2012/059772, mailed Apr. 24, 2014, 5 pages.
Cohen et al., "State-of-the-art reperfusion strategies for acute ischemic stroke," J Clin Neurosci., 2011, 18:319-323.
Davalos, "Thrombolysis in acute ischemic stroke: successes, failures, and new hopes," Cerebrovasc Dis., 2005, 20(Suppl2):135-139.
Flood and Hajjar, "The annexin A2 system and vascular homeostasis," Vascular Pharmacol., 2011, 54:59-67 (Author Manuscript).
Hajjar and Menell, "Annexin II: a novel mediator of cell surface plasmin generation," Ann NY Acad Sci., 1997, 811:337-349 (Abstract Only).
Ishii et al., "Recombinant annexin II modulates impaired fibrinolytic activity in vitro and in rat carotid artery," Circ Res., 2001, 89:1240-1245.
Kaur et al., "The neurotoxicity of tissue plasminogen activator," J Cereb Blood Flow Metab., 2004, 24:945-963.
Kim and Hajjar, "Annexin II: a plasminogen-plasminogen activator coreceptor," Front Biosci., 2002, 7:d341-d348.
Sreekrishna, "Strategies for optimizing protein expression and secretion in the methylotrophic yeast Pichia pastoris," in: R.H. Baltz, G.D. Hegeman, P.L. Skatrud (Eds.), Industrial Microorganism: Basic and Applied Molecular Genetics, Am. Soc. Microbiol., Washington, DC, 1993, pp. 119-126.
Tabata et al., "Expression and purification of recombinant human annexin A2 in Pichia pastoris and utility of expression product for detecting annexin A2 antibody," J Biosci Bioeng. Feb. 2006, 101(2):190-7.
Walvick et al., "Visualization of clot lysis in a rat embolic stroke model: application to comparative lytic efficacy," Stroke, 2011, 42:1110-1115.
Wang et al., "Mechanisms of hemorrhagic transformation after tissue plasminogen activator reperfusion therapy for ischemic stroke," Stroke, 2004, 35:2726-2730.
Woo and Neville Jr., "Separation of bivalent anti-T cell immunotoxin from Pichia pastoris glycoproteins by borate anion exchange," Biotechniques, 2003, 35:392-398.
Woo et al., "Gene optimization is necessary to express a bivalent anti-human anti-T cell immunotoxin in Pichia pastoris," Protein Expr Purif., 2002, 25:270-282.

(Continued)

*Primary Examiner* — Marcela M Cordero Garcia
*Assistant Examiner* — Mindy Newman
(74) *Attorney, Agent, or Firm* — Fish & Richardson P.C.

(57) ABSTRACT

Methods for the expression and purification of non-N-glycosylated human Annexin A2 in yeast, e.g., in *Pichia pastoris*, purified Annexin A2 produced by those methods, and methods of using the Annexin A2.

15 Claims, 6 Drawing Sheets

(56) References Cited

OTHER PUBLICATIONS

Yepes et al., "Tissue-type plasminogen activator in the ischemic brain: more than a thrombolytic," Trends Neurosci., 2009, 32:48-55.
Zhu et al., "Annexin A2 combined with low-dose tPA improves thrombolytic therapy in a rat model of focal embolic stroke," J Cereb Blood Flow Metab., 2010, 30:1137-1146.
SHUNJ1 Takahashi et al. Cloning and Identification of Annexin I I as an Autocrine/Paracrine Factor That Increases Osteoclast Formation and Bone Resorption. The Journal ofBiological Chemistry, Nov. 18, 1994, vol. 269, No. 46, pp. 28696-28701.
Zurina Romay-Penabad et al. Annexin A2 is involved in antiphospholipid antibody-mediated pathogenic effects in vitro and in vivo. Blood, Oct. 1, 2009, vol. 114, No. 14, pp. 3074-3083.
Okabayashi K et al. Secretory production of recombinant urokinase-type plasminogen activator-annexin V chimeras in Pichia pastoris. Gene, Oct. 24, 1996, vol. 177, No. 1-2, pp. 69-76.
International Search Report and Written Opinion mailed Jan. 24, 2013 in International Application No. PCT/US2012/059772, 6 pgs.

* cited by examiner

FIG. 1A

```
atgtctactgttcacgagattttgtgtaagttgtctttggagggtgaccactctactcca
 M  S  T  V  H  E  I  L  C  K  L  S  L  E  G  D  H  S  T  P ccatctgcttacggttctgttaaggcttacactaacttcgacgctgagagagacgctttg
 P  S  A  Y  G  S  V  K  A  Y  T  N  F  D  A  E  R  D  A  L aacattgagactgctattaagactaagggtgttgacgaggttactattgttaacattttg
 N  I  E  T  A  I  K  T  K  G  V  D  E  V  T  I  V  N  I  L actaacagatctaacgctcaaagacaagacattgctttcgcttaccaaagaagaactaag
 T  N  R  S  N  A  Q  R  Q  D  I  A  F  A  Y  Q  R  R  T  K aaggagttggcttctgctttgaagtctgctttgtctggtcacttggagactgttattttg
 K  E  L  A  S  A  L  K  S  A  L  S  G  H  L  E  T  V  I  L ggtttgttgaagactccagctcaatacgacgcttctgagttgaaggcttctatgaagggt
 G  L  L  K  T  P  A  Q  Y  D  A  S  E  L  K  A  S  M  K  G ttgggtactgacgaggactcttttgattgagattatctgttctagaactaaccaagagttg
 L  G  T  D  E  D  S  L  I  E  I  I  C  S  R  T  N  Q  E  L caagagattaacagagtttacaaggagatgtacaagactgacttggagaaggacattatc
 Q  E  I  N  R  V  Y  K  E  M  Y  K  T  D  L  E  K  D  I  I tctgacacttctggtgacttcagaaagttgatggttgctttggctaagggtagaagagct
 S  D  T  S  G  D  F  R  K  L  M  V  A  L  A  K  G  R  R  A gaggacggttctgttattgactacgagttgattgaccaagacgctagagacttgtacgac
 E  D  G  S  V  I  D  Y  E  L  I  D  Q  D  A  R  D  L  Y  D gctggtgttaagagaaagggtactgacgttccaaagtggatttctattatgactgagaga
 A  G  V  K  R  K  G  T  D  V  P  K  W  I  S  I  M  T  E  R tctgttccacacttgcaaaaggttttcgacagatacaagtcttactctccatacgacatg
 S  V  P  H  L  Q  K  V  F  D  R  Y  K  S  Y  S  P  Y  D  M ttggagtctattagaaaggaggttaagggtgacttggagaacgctttcttgaacttggtt
 L  E  S  I  R  K  E  V  K  G  D  L  E  N  A  F  L  N  L  V caatgtattcaaaacaagccattgtacttcgctgacagattgtacgactctatgaagggt
 Q  C  I  Q  N  K  P  L  Y  F  A  D  R  L  Y  D  S  M  K  G aagggtactagagacaaggttttgattagaattatggtttctagatctgaggttgacatg
 K  G  T  R  D  K  V  L  I  R  I  M  V  S  R  S  E  V  D  M ttgaagattagatctgagttcaagagaaagtacggtaagtctttgtactactacattcaa
 L  K  I  R  S  E  F  K  R  K  Y  G  K  S  L  Y  Y  Y  I  Q caagacactaagggtgactaccaaaaggctttgttgtacttgtgtggtggtgacgaccac
 Q  D  T  K  G  D  Y  Q  K  A  L  L  Y  L  C  G  G  D  D  H caccaccaccaccac           SEQ ID NO:3
 H  H  H  H  H            SEQ ID NO:4
```

NON-N-GLYCOSYLATED RECOMBINANT HUMAN ANNEXIN A2

CLAIM OF PRIORITY

This application is a U.S. National Phase Application under 35 U.S.C. §371 of International Patent Application No. PCT/US2012/059772, filed on Oct. 11, 2012, which claims the benefit of U.S. Patent Application Ser. No. 61/546,196, filed on Oct. 12, 2011; the entire contents of the foregoing are hereby incorporated by reference.

TECHNICAL FIELD

This invention relates to methods for the expression and purification of non-N-glycosylated human Annexin A2 in yeast, e.g., in *Pichia pastoris*, purified Annexin A2 produced by those methods, and methods of using the non-N-glycosylated human Annexin A2.

BACKGROUND tPA (Tissue Plasminogen Activator) converts thrombus-bound plasminogen to plasmin, which degrades cross-linked fibrin. tPA is used clinically in the emergency treatment of ischemic stroke, but its use can lead to major complications, including hemorrhagic transformation and neurotoxicity. Furthermore, the tPA must be administered within a short treatment time window of about 2-3 hours after the ischemic event.

Human Annexin A2 is a cell surface receptor for both plasminogen and tPA, and forms a recombinant human Annexin A2 (rA2)-tPA-plasminogen triple complex. Co-administration of Annexin A2 lowers the effective concentration of tPA required to convert plasminogen to plasmin, reduces the risk of neurotoxic and hemorrhagic complications, and prolongs the treatment window. See, e.g., Zhu et al, J. Cereb. Blood Flow Metab. 30:1137-1146 (2010) and US2011/129526.

SUMMARY

The present invention is based, at least in part, on the discovery that biological function of human Annexin A2 expressed in the yeast *Pichia pastoris* can be fully recovered through site-specific mutation to remove the unique N-glycosylation site. Also described herein are uses of the non-N-glycosylated human annexin A2, and a purification protocol developed to separate fully functional forms from partially functional forms.

Thus in one aspect, the invention provides non-N-glycosylated human annexin A2 comprising SEQ ID NO:1, wherein the amino acid at position 62 is not Asparagine (N), and/or the amino acid at position 64 is neither Threonine (T) nor Serine (S). In some embodiments, the amino acid at position 62 is Alanine (A) or Glycine (G).

In another aspect, the invention provides a *Pichia pastoris* codon-optimized nucleic acid molecule (e.g., comprising SEQ ID NO:2) encoding a non-N-glycosylated human annexin A2 described herein. In further aspects, the invention provides vectors comprising said nucleic acid molecules.

In an additional aspect, the invention provides host cells expressing a nucleic acid molecule encoding a non-N-glycosylated human annexin A2 described herein. In some embodiments, the host cell is a methylotropic yeast, e.g., a cell of the species *Pichia Pastoris*.

In yet another aspect, the invention provides pharmaceutical compositions comprising a non-N-glycosylated human annexin A2 described herein and a physiologically acceptable carrier. In some embodiments, the compositions also include another active ingredient, e.g., tissue plasminogen activator (TpA), an anticoagulant (e.g., heparin (such as low molecular weight heparin or unfractionated heparin) or warfarin (e.g., COUMADIN), or a vitamin K antagonist.

In another aspect, the invention provides methods for treating a subject who has had an ischemic stroke; the methods include administering to the subject a therapeutically effective amount of a non-N-glycosylated human annexin A2 as described herein. In some embodiments, the methods further include administering a therapeutically effective amount of TpA to the subject, e.g., before, substantially concurrently with, or after the annexin A2.

Also provided herein is a non-N-glycosylated human annexin for treating ischemic stroke, as well as the use of a non-N-glycosylated human annexin A2 as described herein in the manufacture of a medicament for treating ischemic stroke.

Finally, in a further aspect the invention provides methods for producing a non-N-glycosylated human Annexin A2. The methods include expressing a non-N-glycosylated human annexin A2 comprising SEQ ID NO:1, wherein the amino acid at position 62 is not Asparagine (N), and/or the amino acid at position 64 is neither Threonine (T) nor Serine (S), in a methylotropic yeast; and substantially purifying the non-N-glycosylated human annexin A2, thereby producing the composition. In some embodiments, substantially purifying the non-N-glycosylated human annexin A2 includes contacting a composition comprising non-N-glycosylated human annexin A2 with a strong cation exchange resin; and collecting fractions having higher annexin 2 biological activity.

In some embodiments, the methods include collecting one or both of a flow-through and a washing fraction (e.g., in some embodiments the fractions having the higher activity are the flow-through and washing fractions).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A. Codon-optimized human annexin A2-6×His DNA (SEQ ID NO:3) and derived amino acid sequence (SEQ ID NO:4) for *Pichia pastoris* expression. The unique asparagine (N-linked glycosylation site; shown in the box) was replaced with a non-polarized alanine (N62A) for non-N-glycosylated human annexin A2-6×His.

TT: AOX1 transcription termination region; TEF1: TEF1 promoter region; EM7: EM7 promoter region; Zeocin: Zeocin resistance gene (Sh ble ORF); CYC1: CYC1 transcription termination region; ColE1: ColE1 origin (pUC-derived).

Figure 2A:
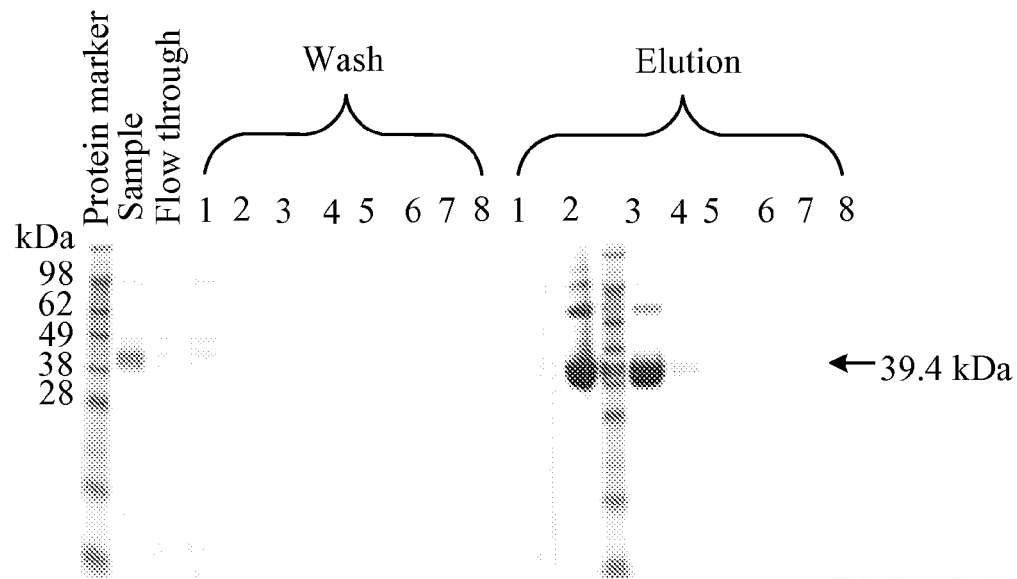
Figure 2B:
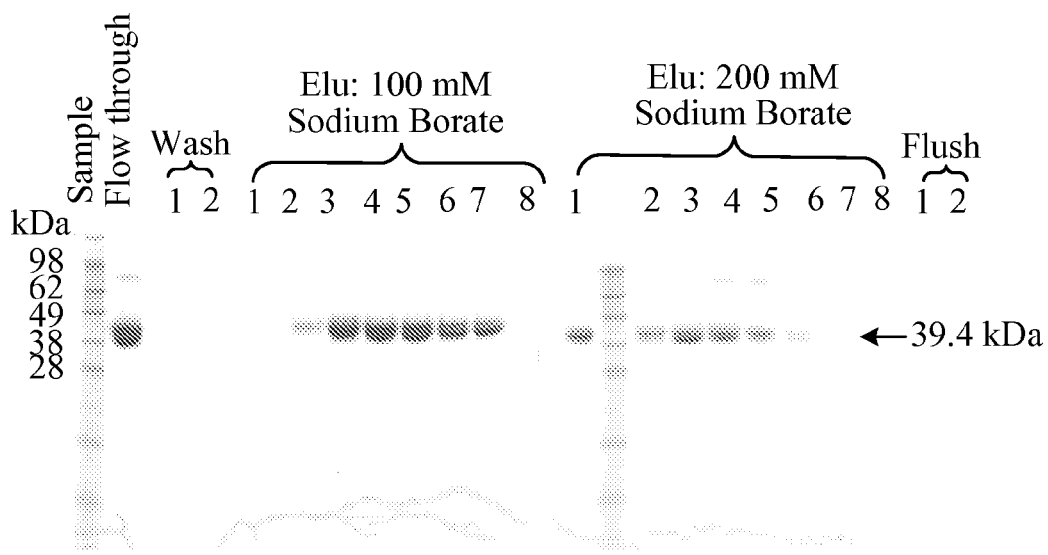

FIGS. 2A-B. Purification of glycosylated human annexin A2: A) First step purification using Ni-Sepharose 6 fast flow resin. Lane 1 and 14: protein markers; Lane 2: sample; Lane 3: flowthrough; Lane 4-11: eight 50 mL washing fractions; Lane 12-13 and 15-20: eight 50 mL elution fractions using 500 mM imidazole. B) Second step purification using strong cation-exchange resin Poros 50HS. Lane 1 and 14: protein markers; Lane 2: sample; Lane 3: flowthrough; Lane 4-5: two 40 mL washing fractions; Lane 6-13: eight 10 mL elution fractions using 50 mM sodium borate; Lane 15-22: eight 10 mL elution fractions using 100 mM sodium borate; Lane 23-24: flushing using 1 M NaCl.

Figure 3A:
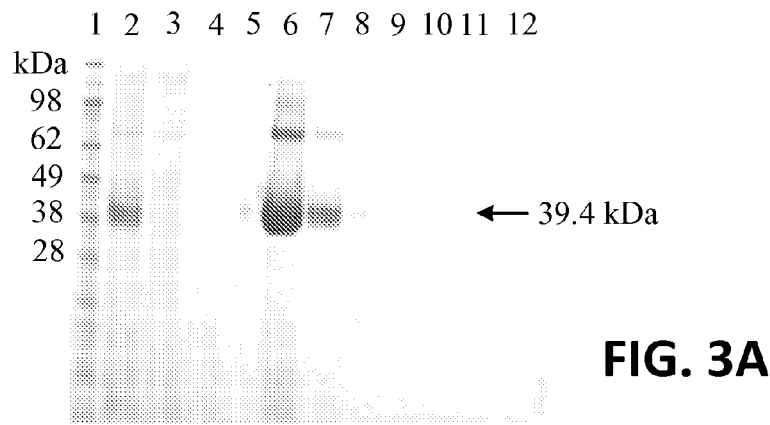
Figure 3B:
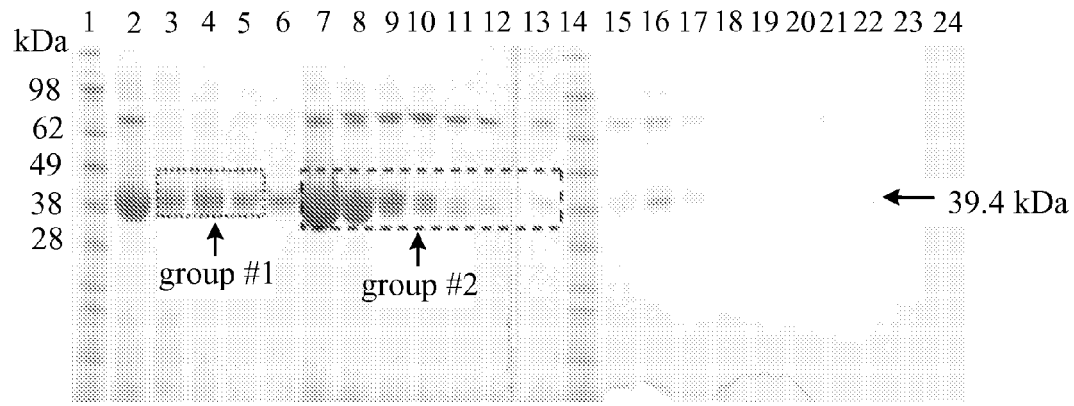
Figure 3C:
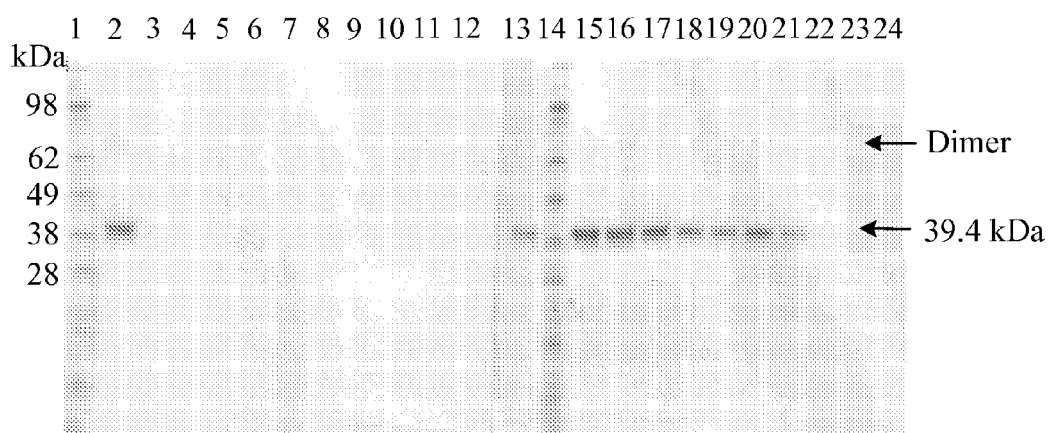

FIGS. 3A-C. Purification of non-N-glycosylated human annexin A2: A) First step purification using Ni-Sepharose 6 fast flow resin. Lane 1: protein markers; Lane 2: sample; Lane 3: flowthrough; Lane 4: 300 mL washing fraction; Lane 5-12: eight 50 mL elution fractions using 500 mM imidazole. B) Second step purification using strong cation-exchange resin Poros 50HS. Lane 1 and 14: protein markers; Lane 2: sample; Lane 3: flowthrough; Lane 4-5: two 40 mL washing fractions; Lane 6-13: eight 10 mL elution fractions using 100 mM sodium borate; Lane 15-22: eight 10 mL elution fractions using 200 mM sodium borate; Lane 23-24: flushing using 1 M NaCl. C) Third step purification for non-N-glycosylated human annexin A2 group#1 using Ni-Sepharose 6 fast flow resin. Lane 1 and 14: protein markers; Lane 2: sample; Lane 3: flowthrough; Lane 4-5: two 40 mL washing fractions; Lane 6-11: six 10 mL elution fractions using 40 mM imidazole; Lane 12-13 and 15-18: six 10 mL elution fractions using 100 mM imidazole; Lane 19-24: elution fractions using 200 mM imidazole. The weak band seen at approximately 80 kDa is a covalent homodimer of the non-N-glycosylated human annexin A2 generated by disulfide bond formation (analyzed under reduced conditions using DTT or beta-mercaptoethanol).

Figure 4:
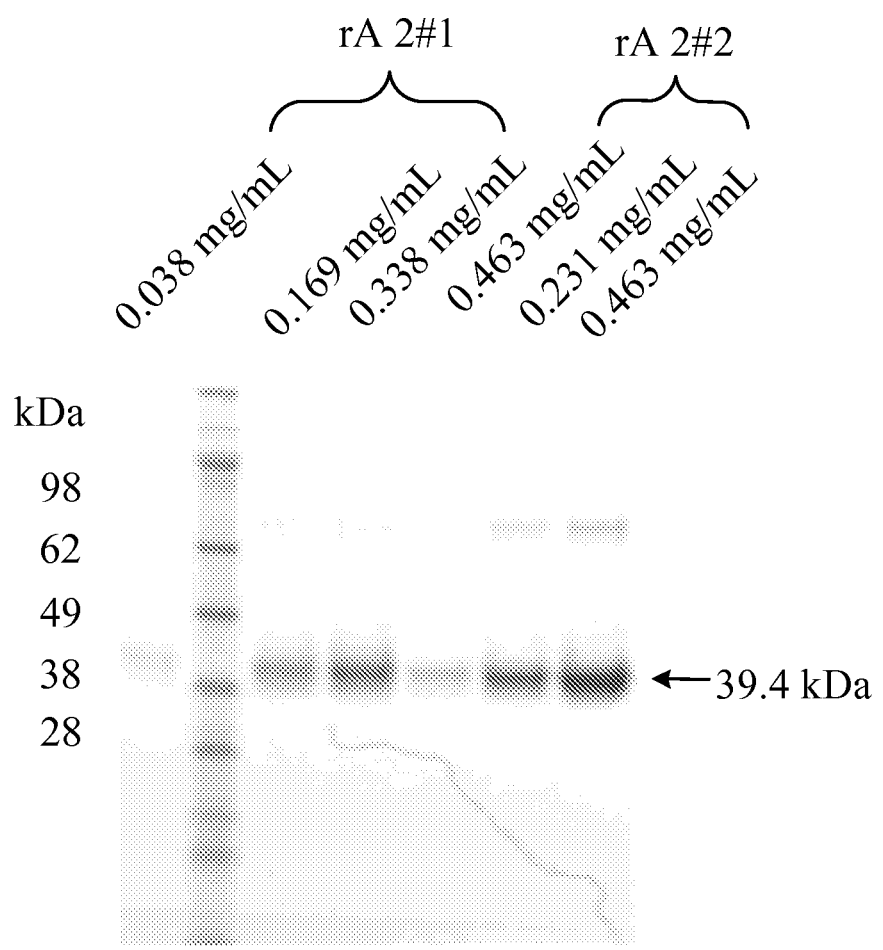

FIG. 4. SDS gel analysis for two groups of the two-step purified non-N-glycosylated human annexin A2. Group#1: rA2#1; group#2: rA2#2.

Figure 5:
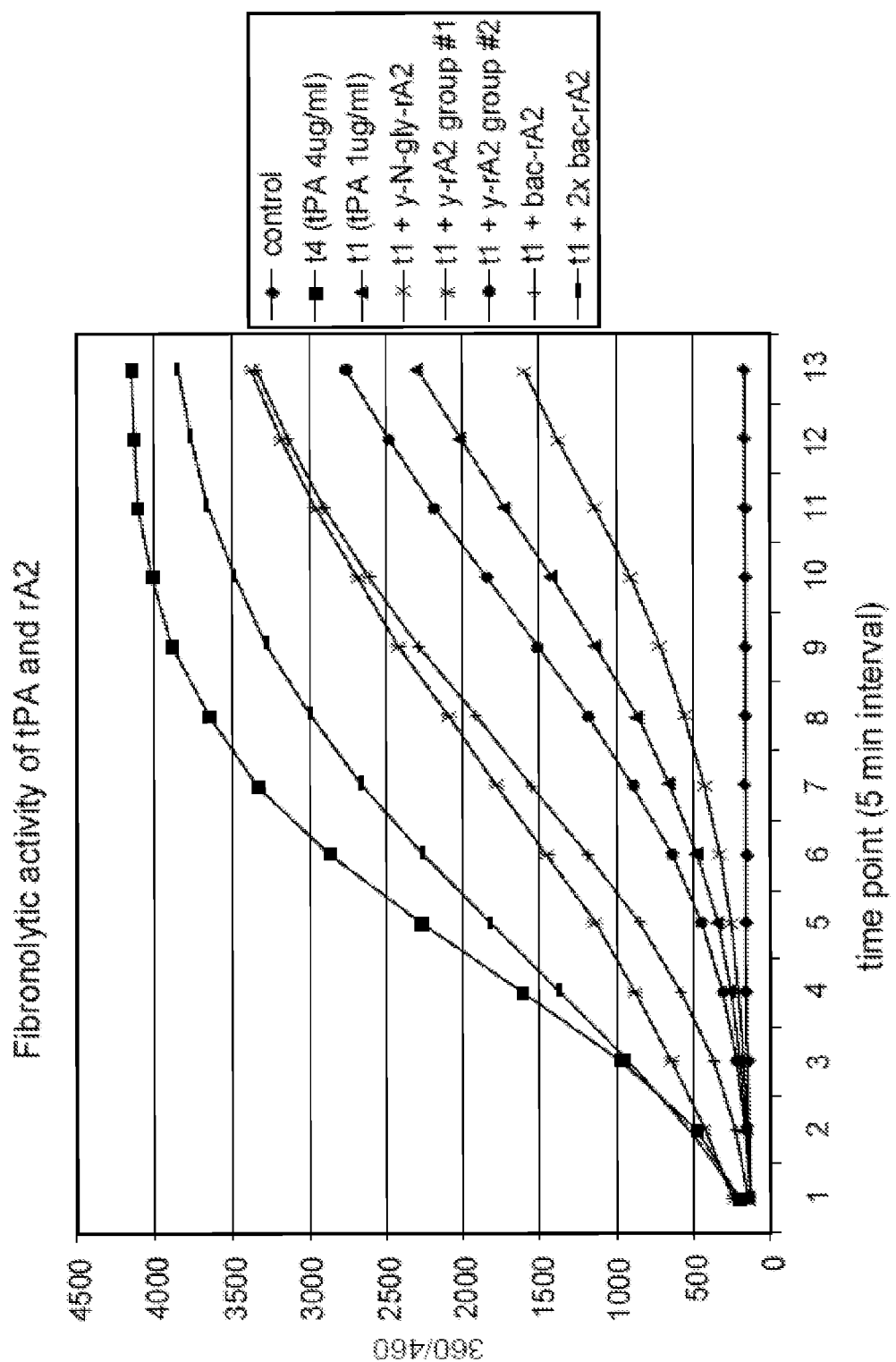

FIG. 5. In vitro amplifying function analysis for tPA-mediated plasmin-generation by glycosylated and non-N-glycosylated human annexin A2. Control: negative control; t4: 4 μg/mL of tPA control; t1: 1 μg/mL of tPA control; t1+y-N-gly-rA2: 1 μg/mL of tPA+2 μg/mL of glycosylated human annexin A2 expressed in yeast; t1+y-rA2 group #1: 1 μg/mL of tPA+2 μg/mL of non-N-glycosylated human annexin A2 group#1 expressed in yeast; t1+y-rA2 group #2: 1 μg/mL of tPA+2 μg/mL of non-N-glycosylated human annexin A2 group#2 expressed in yeast; t1+bac-rA2: 1 μg/mL of tPA+2 μg/mL of E. coli expressed human annexin A2 as positive control; t1+2×bac-rA2: 1 μg/mL of tPA+2×2 μg/mL of E. coli expressed human annexin A2 as positive control.

DETAILED DESCRIPTION

Normally, thrombosis (clot formation) limits hemorrhage caused by vascular injury, and is held in check by antithrombotic properties and fibrinolysis. Non-pathological thrombi are confined to the immediate area of an injury and do not obstruct blood flow to critical areas. However, under pathological conditions, a thrombus can obstruct blood flow in vessels narrowed by atherosclerotic plaques; or can propagate into otherwise normal vessels, obstructing flow in critical blood vessels or obliterating valves and other structures essential to normal blood flow and hemodynamic function. The results can include acute myocardial infarction (AMI), deep vein thrombosis, pulmonary embolism, acute ischemic stroke, acute peripheral arterial occlusion, and occlusion of indwelling catheters.

Thrombosis depends on the action of platelets, thrombin, and fibrin. Activated platelets aggregate at the injury site and activate circulating prothrombin to the clotting factor, thrombin, which in turn activates fibrinogen to fibrin, which forms a fibrin matrix that traps plasminogen and makes the thrombus more resistant to thrombolysis. Pathological thrombosis can occur in any vessel at any location in the body. Risk factors for thrombosis include changes in blood flow; metabolic disorders such as the metabolic syndrome, diabetes mellitus, and hyperlipidemia; atherosclerosis; hypercoagulable states; smoking; and trauma, including burns.

Thrombolytic agents presently in use, including tPA, work by converting plasminogen to the fibrinolytic agent plasmin, which lyses the thrombus by breaking down fibrinogen and fibrin.

Intravenous tPA administration within 3 hours of a stroke is the only USFDA approved thrombolytic agent for acute ischemic stroke (Cohen et al., 2011). The tPA converts thrombus-bound plasminogen to plasmin to degrade cross-linked fibrin. Clinical complications limiting tPA treatment include hemorrhagic transformation, neurotoxicity and short treatment window (Kaur et al., 2004; Wang et al., 2004; Yepes et al., 2009). Therefore improved tPA stroke therapy is needed in the field (Davalos, 2005).

Annexin A2 is an endothelial cell surface receptor for both plasminogen and tPA and facilitates the generation of plasmin. Clinically, large doses of tPA are required to overcome the circulating protease inhibitors. The recombinant human annexin A2-tPA-plasminogen triple complex can lower the concentration of tPA required to convert plasminogen to plasmin (Hajjar and Menell, 1997, Kim and Hajjar 2002; see also US2011/129526). It seems that annexin A2 is able to protect tPA from its major antagonist, plasminogen inhibitor-1. It was recently reported that *E. coli* expressed recombinant human annexin A2 as an enhancer was combined with low dose tPA to improve thrombolytic therapy in a rat focal embolic stroke model; the tPA dose was reduced for four-fold, brain infarction, and hemorrhagic transformation were reduced, and the time window for stroke reperfusion was prolonged (Zhu et al., 2010). MRI-based clot imaging in this rat focal embolic stroke model also documented that tPA plus *E. coli*-expressed recombinant human annexin A2 yield faster and more consistent thrombolysis than tPA alone (Walvick et al., 2011). However, it was very difficult to purify the *E. coli*-expressed human annexin A2.

Wild-type human annexin A2 has been expressed in yeast *Pichia pastoris* system (see, e.g., Tabata et al., J Biosci Bioeng. 2006 February; 101(2):190-7). However, the biological activity of the Annexin 2 produced in this manner was dramatically decreased (see FIG. 5). The present inventors hypothesized that the function loss was due to the high-mannose glycosylation mechanisms of the yeast *pichia pastoris*. Therefore site-specific mutagenesis was used to alter the N-glycosylation site at amino acid 62 in human annexin A2 cDNA. Surprisingly, though the mutated residue is highly conserved across species, the *pichia pastoris*-expressed non-N-glycosylated human Annexin A2 was fully biologically functional.

Annexin A2

Human Annexin A2 is a protein of about 339 amino acids, and the mature protein produced in human cells has a weight of about 38.6 kDa and a PI=8.86. It is a calcium-dependent phospholipid-binding protein; presently, its sole known function is in fibrinolysis Annexin A2 functions as an autocrine factor which heightens osteoclast formation and bone resorption.

The wild type gene has four variants, as follows:

| Variant | Nucleic Acid | Protein | Comments |
|---|---|---|---|
| annexin A2 isoform 1 | NM_001002858.2 | NP_001002858.1 | This variant (1) encodes the longer isoform (1) |
| annexin A2 isoform 2 (Variants 2, 3 and 4 use a downstream AUG start codon; all encode the same isoform (2) which has a shorter N-terminus, as compared to isoform 1. | NM_001002857.1 | NP_001002857.1 | variant (2) has an alternate 5' UTR, as compared to variant 1. It uses a downstream AUG start codon and encodes isoform 2 |
| | NM_004039.2 | NP_004030.1 | variant (3) lacks a segment in the 5' region, as compared to variant 1. |
| | NM_001136015.2 | NP_001129487.1 | variant (4) has an alternate 5' UTR, as compared to variant 1. |

In some embodiments, the mutated human Annexin 2 polypeptide sequences used in the present methods and compositions differ from the wild type sequence at least in having a mutation at N62 that removes the N-glycosylation site at that position, shown as an X in the following SEQ ID NO:1.

```
                                            SEQ ID NO: 1
                                            SEQ ID NO: 1
   M S T V H E I L C K L S L E G D H S T P    20
   P S A Y G S V K A Y T N F D A E R D A L    40
   N I E T A I K T G V D E V T I V N I L      60
   T X R X N A Q R Q D I A F A Y Q R R T K    80
   K E L A S A L K S A L S G H L E T V I L    100
   G L L K T P A Q Y D A S E L K A S M K G    120
   L G T D E D S L I E I I C S R T N Q E L    140
   Q E I N R V Y K E M Y K T D L E K D I I    160
   S D T S G D F R K L M V A L A K G R R A    180
   E D G S V I D Y E L I D Q D A R D L Y D    200
   A G V K R K G T D V P K W I S I M T E R    220
   S V P H L Q K V F D R Y K S Y S P Y D M    240
   L E S I R K E V K G D L E N A F L N L V    260
   Q C I Q N K P L Y F A D R L Y D S M K G    280
   K G T R D K V L I R I M V S R S E V D M    300
   L K I R S E F K R K Y G K S L Y Y Y I Q    320
       Q D T K G D Y Q K A L L Y L C G G D D  339
```

The mutation at N62 can be to any amino acid other than N, so long as the mutation substantially preserves the fibrinolytic mediating function, or the ability to enhance tPA-mediated plasmin-generation, of the molecule, i.e., the mutant retains at least 20% of the function of the wild type molecule, e.g., at least 30%, 40%, 50%, 60%, 70%, 80%, 90%, 95%, or more of the function of the wild type molecule, e.g., in an in vitro assay as known in the art or described herein. In some embodiments, the mutation at N62 is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III of US20110201052; pages 13-15 "Biochemistry" 2.sup.nd ED. Lubert Stryer ed (Stanford University); Henikoff et al., PNAS 1992 Vol 89 10915-10919; Lei et al., J Biol Chem 1995 May 19; 270(20):11882-6). In some embodiments, the mutation at N62 is to alanine or glycine. In some embodiments, the mutation at N62 is a glutamine. In some embodiments, the mutation at N62 is an aspartate or glutamate.

In some embodiments, instead of or in addition to a mutation at N62, the mutant A2 includes a mutation at T64 to any amino acid other than serine or threonine, thereby disrupting the N-linked glycosylation consensus site. In some embodiments, the mutation at T64 is a conservative substitution, e.g., to serine; in some embodiments, the mutation is to alanine or glycine.

In some embodiments, the sequences further include a peptide tag useful for purification. In some embodiments, the tag comprises histidines, e.g., two or more, e.g., three, four, five or six histidine residues at the C-terminus (i.e., as shown at positions 400-405 of SEQ ID NO:4, FIG. 1), and purification is achieved by binding to a nickel or cobalt column. In some embodiments, the tag comprises glutathione-S-transferase (GST) and recovery is by affinity to substrate glutathione bound to a column, e.g. glutathione sepharose. In some embodiments, the tag comprises a FLAG peptide (e.g., N-DYKDDDDK-C(SEQ ID NO:5) or a variant therof) and protein is recovered with specific antibody to the peptide. In some embodiments, the tag comprises an epitope derived from the Influenza protein haemagglutinin (HA) (e.g., N-YPYDVP-C (SEQ ID NO:6)) and protein is recovered using an anti-HA antibody that binds the epitope. In some embodiments, the tag comprises an epitope derived from the human proto-oncoprotein myc (e.g., N-ILKKATAYIL-C (SEQ ID NO:7), or N-EQKLISEEDL-C(SEQ ID NO:8)), and recovery is performed with an anti-myc antibody.

In some embodiments, the protein further comprises a proteolytic cleavage site between the purification tag and the annexin A2 sequence, and after purification the protein is treated with the protease to remove the purification tag. Examples include the PreScission protease, thrombin, and factor Xa. Enterokinase sites that enable tag cleavage without leaving behind extra amino acids are preferred. In some embodiments, an exopeptidase is used to remove N-terminal His-tags (e.g., Qiagen TAGZyme). See, e.g., *The Recombinant Protein Handbook, Protein Amplification and Simple Purification*, Amersham Biosciences, available online at 130.15.90.245/methods/hand-books%20and%20manuals/the%20recombinant%20protein%20handbook.pdf.

Codon Optimization

In addition, the nucleic acid sequences used in the present methods is preferably codon-optimized for expression in a selected expression system, e.g., in *pichia pastoris* (See, e.g., Woo et al., 2002). In order to optimize expression in non-mammalian cells, codon optimization specific for a selected host organism can be used. For example, in embodiments where *P. pastoris* is used as a host organism, the following Table 1 (source: kazusa.or.jp) can be used to select codons:

TABLE 1

Codon Optimization Table for *Pichia Pastoris*

| triplet | UUU | UCU | UAU | UGU |
|---|---|---|---|---|
| amino acid | F | S | Y | C |
| fraction | 0.54 | 0.29 | 0.47 | 0.64 |
| frequency: per 1000 | 24.1 | 24.4 | 16.0 | 7.7 |
| (number) | (1963) | (1983) | (1300) | (626) |
| triplet | UUC | UCC | UAC | UGC |
| amino acid | F | S | Y | C |
| fraction | 0.46 | 0.20 | 0.53 | 0.36 |
| frequency: per 1000 | 20.6 | 16.5 | 18.1 | 4.4 |
| (number) | (1675) | (1344) | (1473) | (356) |
| triplet | UUA | UCA | UAA | UGA |
| amino acid | L | S | * | * |
| fraction | 0.16 | 0.18 | 0.51 | 0.20 |
| frequency: per 1000 | 15.6 | 15.2 | 0.8 | 0.3 |
| (number) | (1265) | (1234) | (69) | (27) |
| triplet | UUG | UCG | UAG | UGG |
| amino acid | L | S | * | W |
| fraction | 0.33 | 0.09 | 0.29 | 1.00 |
| frequency: per 1000 | 31.5 | 7.4 | 0.5 | 10.3 |
| (number) | (2562) | (598) | (40) | (834) |
| triplet | CUU | CCU | CAU | CGU |
| amino acid | L | P | H | R |
| fraction | 0.16 | 0.35 | 0.57 | 0.17 |
| frequency: per 1000 | 15.9 | 15.8 | 11.8 | 6.9 |
| (number) | (1289) | (1282) | (960) | (564) |
| triplet | CUC | CCC | CAC | CGC |
| amino acid | L | P | H | R |
| fraction | 0.08 | 0.15 | 0.43 | 0.05 |
| frequency: per 1000 | 7.6 | 6.8 | 9.1 | 2.2 |
| (number) | (620) | (553) | (737) | (175) |
| triplet | CUA | CCA | CAA | CGA |
| amino acid | L | P | Q | R |
| fraction | 0.11 | 0.42 | 0.61 | 0.10 |
| frequency: per 1000 | 10.7 | 18.9 | 25.4 | 4.2 |
| (number) | (873) | (1540) | (2069) | (340) |

TABLE 1 -continued

Codon Optimization Table for *Pichia Pastoris*

| triplet | CUG | CCG | CAG | CGG |
|---|---|---|---|---|
| amino acid | L | P | Q | R |
| fraction | 0.16 | 0.09 | 0.39 | 0.05 |
| frequency: per 1000 | 14.9 | 3.9 | 16.3 | 1.9 |
| (number) | (1215) | (320) | (1323) | (158) |
| triplet | AUU | ACU | AAU | AGU |
| amino acid | I | T | N | S |
| fraction | 0.50 | 0.40 | 0.48 | 0.15 |
| frequency: per 1000 | 31.1 | 22.4 | 25.1 | 12.5 |
| (number) | (2532) | (1820) | (2038) | (1020) |
| triplet | AUC | ACC | AAC | AGC |
| amino acid | I | T | N | S |
| fraction | 0.31 | 0.26 | 0.52 | 0.09 |
| frequency: per 1000 | 19.4 | 14.5 | 26.7 | 7.6 |
| (number) | (1580) | (1175) | (2168) | (621) |
| triplet | AUA | ACA | AAA | AGA |
| amino acid | I | T | K | R |
| fraction | 0.18 | 0.24 | 0.47 | 0.48 |
| frequency: per 1000 | 11.1 | 13.8 | 29.9 | 20.1 |
| (number) | (906) | (1118) | (2433) | (1634) |
| triplet | AUG | ACG | AAG | AGG |
| amino acid | M | T | K | R |
| fraction | 1.00 | 0.11 | 0.53 | 0.16 |
| frequency: per 1000 | 18.7 | 6.0 | 33.8 | 6.6 |
| (number) | (1517) | (491) | (2748) | (539) |
| triplet | GUU | GCU | GAU | GGU |
| amino acid | V | A | D | G |
| fraction | 0.42 | 0.45 | 0.58 | 0.44 |
| frequency: per 1000 | 26.9 | 28.9 | 35.7 | 25.5 |
| (number) | (2188) | (2351) | (2899) | (2075) |
| triplet | GUC | GCC | GAC | GGC |
| amino acid | V | A | D | G |
| fraction | 0.23 | 0.26 | 0.42 | 0.14 |
| frequency: per 1000 | 14.9 | 16.6 | 25.9 | 8.1 |
| (number) | (1210) | (1348) | (2103) | (655) |
| triplet | GUA | GCA | GAA | GGA |
| amino acid | V | A | E | G |
| fraction | 0.15 | 0.23 | 0.56 | 0.33 |
| frequency: per 1000 | 9.9 | 15.1 | 37.4 | 19.1 |
| (number) | (804) | (1228) | (3043) | (1550) |
| triplet | GUG | GCG | GAG | GGG |
| amino acid | V | A | E | G |
| fraction | 0.19 | 0.06 | 0.44 | 0.10 |
| frequency: per 1000 | 12.3 | 3.9 | 29.0 | 5.8 |
| (number) | (998) | (314) | (2360) | (468) |

Protein Production Methods

The methods for producing non-N-glycosylated human annexin A2 described herein can be performed using protein production methods known in the art. For example, for scaled-up production, fermentation expression can be used.

Yeast *Pichia pastoris* has been widely utilized to express heterologous recombinant proteins as its expression yield is high and the downstream purification is friendly as the protein of interest is secreted into the medium (Cregg, Methods Mol. Biol. 389 (2007) 1-10; Brondyk, Methods Enzymol. 463 (2009) 131-147).

Furthermore, although in a preferred embodiment the present methods use *P. pastoris* as a host organism, e.g., wild-type, X33, GS115 (his4), KM71, MC100-3, SMD1163, SMD1165, or SMD1168 strain, others can also be used. For example, mutant strains of *P. pastoris* that have been altered to express proteins with more human-like glycosylation can be used (see, e.g., Bollok et al., Recent Patents on Biotechnology 2009, 3, 192-201; U.S. Pat. Nos. 7,029,872; 6,803, 225; 7,449,308; 7,252,933; 7,326,681; 7,507,573; and references described therein); in such methods, either the wild-type human annexin A2 or the mutated human annexin A2 can be used. Other yeast, e.g., other methylotropic yeast, e.g., yeast of the genera *Candida, Hansenula* or *Torulopsis*, can also be used. Generally speaking, most *P. pastoris* expression strains are derivatives of NRRL-Y 11430 (Northern Regional Research Laboratories, Peoria, Ill.).

Vectors suitable for use in the present methods are known in the art, and generally include a promoter, e.g., an AOX1, a constitutive *P. pastoris* promoter derived from the *P. pastoris* glyceraldehyde-3-phosphate dehydrogenase gene (GAP) promoter, typically followed immediately with a DNA sequence that encodes a secretion signal, e.g., the *S. cerevisiae* α factor prepro signal sequence, or the signal sequence derived from the *P. pastoris* acid phosphatase gene (PHO1).

The vectors can also include one or more yeast selectable markers that can be used to identify and/or select those cells that contain the vector can be used. Such markers can include drug resistance markers and pathways for synthesis of essential cellular components, e.g., nutrients. Drug resistance markers that can be used in yeast include chloramphenicol, kanamycin, methotrexate, G418 (geneticin), Zeocin, and the like. Markers in synthesis pathways can be used with available yeast strains having auxotrophic mutations in the corresponding gene; examples include the pathways for synthesizing leucine (LEU2), tryptophan (TRP1 and TRP2), proline (PROD, uracil (URA3, URA5, URA6), histidine (HIS3), lysine (LYS2), adenine (ADEJ or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al, J. Biol. Chem. 272: 30061-30066 (1997)). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. Nos. 7,479,389, 7,514,253, U.S. Published Application No. 2009012400, and WO2009/085135). Examples of insertion sites include, but are not limited to, *Pichia* ADE genes; *Pichia* TRP (including TRP J through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al, Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X5 180. See e.g., WO2011046855; Cregg, J. M. (2007) *Methods in Molecular Biology: Pichia Protocols*, Second Edition, Volume 389, Humana Press, Totowa, N.J.; Romanos et al., Yeast 8:423-488 (1992); Ilgen, et al., (2004) Chapter 7: *Pichia pastoris*. In: *Production of recombinant proteins: microbial and eukaryotic expression systems*. Gellissen, G. (ed.) Wiley-VCH Verlag, Weinheim, Germany, pp. 143-162; Cereghino and Cregg, FEMS Microbiology Reviews 24:45-66 (2000); and Cregg, "The *Pichia* System", available online at pichia.com/pichia_system.pdf. Exemplary vectors include pPIC3K, pPIC9K, pAO815 and the pPICZ vector series.

Purification

Methods known in the art can be used for nickel-based purification of the non-N-glycosylated human annexin A2. For example, although the present examples use a hexahistidine tag to facilitate purification, this may not be preferred for a pharmaceutical intended for in vivo use. Thus, other methods, including ammonium sulfate precipitation, reversed phase chromatography, hydrophobic interaction chromatography (HIC), size exclusion chromatography, ion exchange chromatography, affinity chromatography, metal binding, immunoaffinity chromatography, HPLC, or purification tags (e.g., as described above) may be used to directly capture the non-N-glycosylated human annexin A2. See, e.g., Deutscher, M. P. (1990) Guide to Protein Purification. In: *Methods in Enzymology* (J. N. Abelson and M. I. Simon, eds.) Academic Press, San Diego, Calif.; and *The Recombinant Protein Handbook, Protein Amplification and Simple Purification*, Amersham Biosciences, available online at 130.15.90.245/methods/hand-books%20and%20manuals/the%20recombinant%20protein%20handbook.pdf.

After purification, the protein can optionally be concentrated, e.g., by lyophilization or ultrafiltration.

Methods of Use—Treating Vascular Disorders

Non-N-glycosylated human Annexin A2 produced using the methods described herein can be used in the treatment of vascular disorders, e.g., disorders associated with thrombus formation, e.g., ischemic stroke, cerebral venous thrombosis (CVT), myocardial infarction (MI), deep vein thrombosis (DVT), pulmonary embolism (PE), peripheral arterial disease (PAD), and blocked catheters; and hematovascular diseases, e.g., acute promyelocytic leukemia (APL), antiphospholipid syndrome (APS); see, e.g., Flood and Hajjar, Vascular Pharmacology 54 (2011) 59-67, incorporated by reference herein, and US PG PUB No. 2011/0129526 to Wang et al., incorporated by reference herein; as well as Low Density Lipoprotein Receptor (LDLR)-associated diseases (e.g., hypercholesterolemia), Very Low Density Lipoprotein Receptor (VLDLR)-associated diseases, and Apolipoprotein E Receptor 2 (ApoER2)-associated diseases (e.g., fetal growth restriction), see US PG PUB No. 2011/0118181 to Seidah et al., incorporated by reference herein. Generally, the methods include administering a therapeutically effective amount of non-N-glycosylated human Annexin A2 as described herein, alone or in combination with tPA, to a subject who is in need of, or who has been determined to be in need of, such treatment.

Stroke is the third leading cause of death and the leading cause of adult disability in the United States, and was the second most common cause of death worldwide in 1999. Strokes (sometimes also referred to as cerebrovascular accidents (CVAs)), are classified into two major types: brain ischemia as a result of thrombosis (a clot formed in an artery leading to an area of the brain), embolism (a clot forms elsewhere and lodges in an artery leading to an area of the brain), or systemic hypoperfusion; and brain hemorrhage due to intracerebral hemorrhage or subarachnoid hemorrhage. These two types of stroke result from diametrically opposite conditions: hemorrhage is caused by the presence of too much blood within the closed cranial cavity, while ischemia is the result of too little blood to supply adequate amounts of nutrients and oxygen to a part of the brain. See, e.g., Caplan L R. Basic pathology, anatomy, and pathophysiology of stroke. In: Caplan's Stroke: A Clinical Approach, 4th ed, Saunders Elsevier, Philadelphia 2009. p. 22; Caplan, L R, Manning, W (Eds). Brain embolism, Informa Healthcare, New York 2006; Caplan L R. Brain embolism, revisited. Neurology 1993; 43:1281; and Caplan, L R. Brain embolism. In: Clinical Neurocardiology, Caplan, L R, Hurst, J W, Chimowitz, M (Eds), Marcel Dekker, New York 1999. p. 35. The present methods can include the use of a combination of tPA plus the Non-N-glycosylated human Annexin A2 produced using the methods described herein, e.g., for the treatment of vascular diseases as described in US PG PUB No. 2011/0129526 to Wang et al., incorporated by reference herein in its entirety.

The present methods can also be used to treat subjects who have had a MI, e.g., subjects with evidence of ST-segment elevation myocardial infarction (STEMI) or presumably new left bundle branch block (LBBB). Patients with STEMI usually have complete occlusion of an epicardial coronary vessel caused by an acute thrombotic obstruction (2005 American Heart Association Guidelines for Cardiopulmonary Resuscitation and Emergency Cardiovascular Care. Part 8: Stabilization of the Patient with Acute Coronary Syndromes. Circulation. Dec. 13 2005; 112(Suppl IV):IV-89-IV-110).

Deep vein thrombosis (DVT), which occurs when form in the extremities, can also be treated using the present methods. Pulmonary embolism (PE) can occur when a fragment of a thrombus in an extremity breaks off and travels to the lungs; the present methods can also be used to treat (PE). The annual incidence of venous thromboembolism (VTE) in the United States is 600,000 cases. Early diagnosis and treatment is crucial to prevent morbidity and mortality. Death from DVT is typically attributed to massive pulmonary embolism.

Central venous access devices (CVADs) are often crucial to successful treatments of chronic diseases, e.g., cancers, that require ongoing venous access and regular maintenance. Thrombotic occlusion of CVADs can be treated using the present methods.

Peripheral vascular disease (PCD) including peripheral arterial disease (PAD) manifests as insufficient tissue perfusion caused by existing atherosclerosis that may be acutely compounded by either emboli or thrombi, and has the potential to cause loss of limb or even loss of life. Although peripheral vascular disease can be a chronic condition, acute limb ischemia can be life threatening and can require emergency intervention, e.g., using the methods described herein, to minimize morbidity and mortality.

For additional information regarding these conditions and their treatment, e.g., other treatments that could be administered in conjunction with the present methods, see Rivera-Bou et al., "Thrombolytic Therapy in Emergency Medicine"

As used in this context, to "treat" means to ameliorate at least one symptom of the vascular disorder. Generally speaking, a treatment will result in the dissolution of the blockage or thrombus and a return or approach to normal blood perfusion.

Often, an ischemic stroke results in a deficit in one or more measures of brain function including level of consciousness; task performance; motor function, e.g., weakness or loss of movement in arms, legs, and hands; visual function; palsy, e.g., facial palsy; ataxia, e.g., limb ataxia; loss of balance or coordination; language fluency, e.g., lack of understanding, aphasia or dysarthria; sensory, e.g., numbness/loss of sensation including pain sensing; confusion; attention, e.g., extinction or inattention; or severe headache. Thus, a treatment can result in an improvement in one or more of these symptoms, and a return or approach to normal brain function. In some embodiments, the subject is evaluated using the National Institutes of Health Stroke Scale (NIHSS), a systematic assessment tool to quantitatively measure stroke-related neurologic deficit, and a treatment with a non-N-glycosylated human Annexin A2 as described herein results in an improvement in one or more items in the NIHSS scale, or in the total score. Other methods of assessment can also be used, e.g., prehospital stroke assessment tools (e.g., Cincinnati Stroke Scale, Los Angeles Prehospital Stroke Screen (LAPSS), or ABCD Score); acute assessment scales (Canadian Neurological Scale (CNS), European Stroke Scale, Glasgow Coma Scale (GCS), Hemispheric Stroke Scale, Hunt & Hess Scale, Mathew Stroke Scale, NIH Stroke Scale (NIHSS), Orgogozo Stroke Scale, Oxfordshire Community Stroke Project Classification (Bamford), Scandinavian Stroke Scale, or World Federation of Neurological Surgeons Grading System for Subarachnoid Hemorrhage Scale); or functional assessment scales (e.g., Berg Balance Scale; Lawton IADL Scale; Modified Rankin Scale; Stroke Impact Scale (SIS); or Stroke Specific Quality of Life Measure (SS-QOL)), and a treatment with a non-N-glycosylated human Annexin A2 as described herein can result in an improvement in one or more items in the scale, or in the total score.

Pharmaceutical Compositions and Methods of Administration

The methods described herein include the manufacture and use of pharmaceutical compositions, which include non-N-glycosylated human Annexin A2 as described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., TpA, an anticoagulant (e.g., heparin (such as low molecular weight heparin or unfractionated heparin) or warfarin (e.g., COUMADIN), or a vitamin K antagonist. Thus the present invention can include compositions comprising both a non-N-glycosylated human Annexin A2 as described herein and an additional active agent, e.g., in therapeutically relevant or effective amounts. In some embodiments, the non-N-glycosylated human Annexin A2 as described herein and the additional agent, e.g., TpA, are present in a ratio of 1:1, 2:1, 3:1, 4:1, or 5:1. An optimal ratio can be determined using methods known in the art, e.g., as described in US2011/129526, which is incorporated herein by reference in its entirety.

Pharmaceutical compositions are typically formulated to be compatible with its intended route of administration. Examples of routes of administration include parenteral, e.g., intravenous, intradermal, intramuscular, subcutaneous, oral (e.g., inhalation), transdermal (topical), and transmucosal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™

(BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1

Plasmid Construction for the Glycosylated and Non-N-glycosylated Human Annexin A2

Figure 1B:
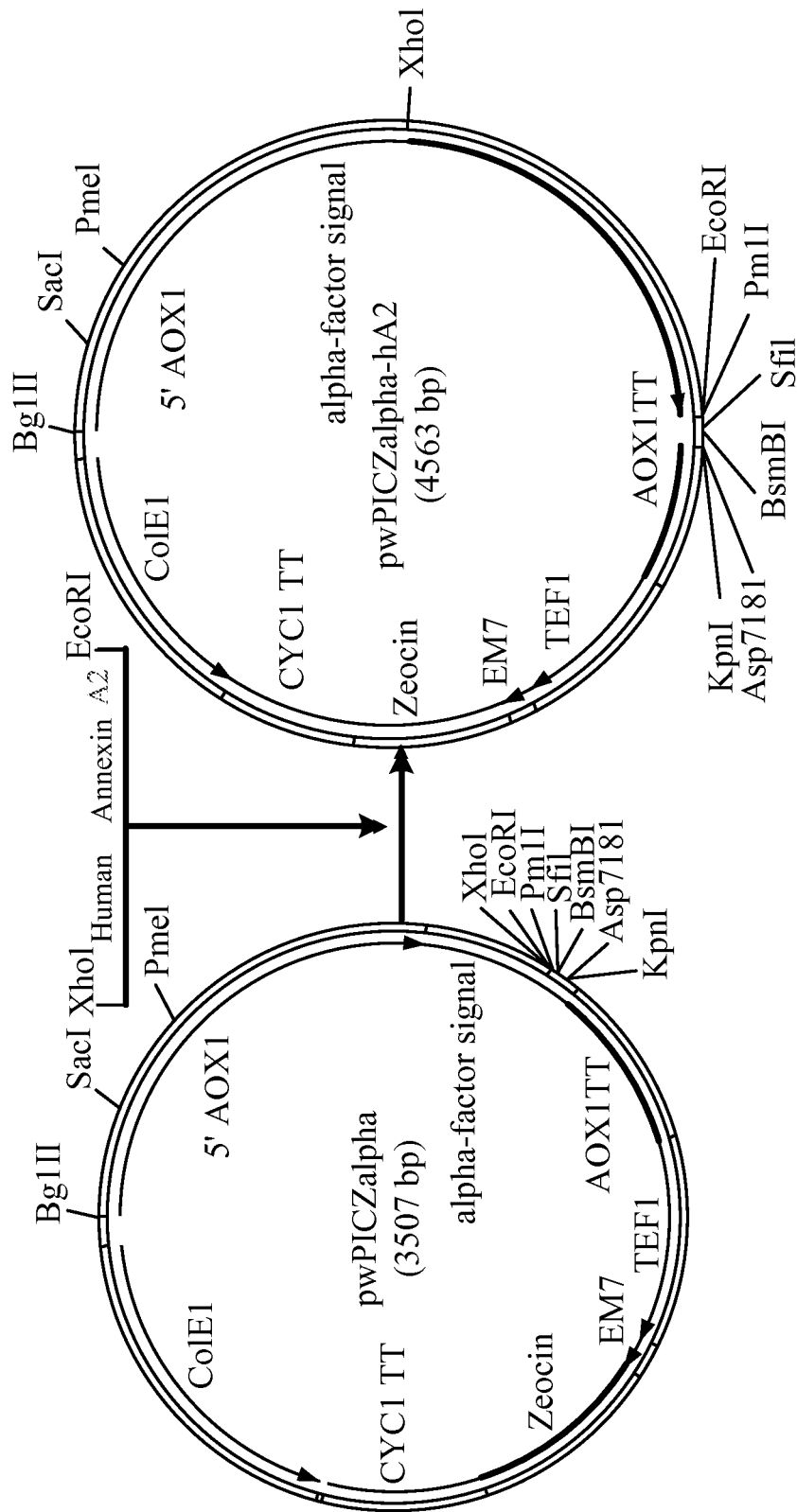
FIG. 1B. Construction of the glycosylated or non-N-glycosylated human annexin A2-6×His (hA2) into pwPICZalpha between XhoI and EcoRI sites. pwPICZalpha was derived from the pPICZalpha vector (Invitrogen). pwPICZalpha contains a unique XhoI site and the original BamHI and NcoI sites were removed by mutation. AOX1: AOX1 region; AOX1

A codon-optimized glycosylated human annexin A2 gene (339 aa) carrying 6×His tag in the C-terminus (sequence in FIG. 1A) was synthesized and cloned into a yeast *Pichia pastoris* expression vector pwPICZalpha (Woo et al., 2002; FIG. 1B). A 6×His tag in the C-terminus was added to facilitate downstream purification. The plasmid construction for a non-N-glycosylated human annexin A2 was exactly same except for that the unique N-glycosylation site in the human annexin A2 gene was replaced with non-polar amino acid alanine (N62A).

Briefly, glycosylated human annexin A2 (339 amino acids) (UniProtKB/Swiss-Prot P07355) was synthesized with the *Pichia pastoris* preferred codons (Sreekrishna 1993) by GenScript. To facilitate the downstream purification, six histidines (6×His tag) were added at the C-terminus. The synthesized human annexin A2 carrying 6×His tag at the C-terminus was sub-cloned into a *Pichia pastoris* expression vector pwPICZalpha (Woo et al., 2002) between XhoI and EcoRI restriction sites. To construct a non-N-glycosylated human annexin A2, the unique asparagine (N-linked glycosylation site) was replaced with non-polarized alanine (N62A in bold in FIG. 1, and bold and caps in SEQ ID NO:2, below) using a site-directed mutagenesis kit (Stratagene) following the manufacturer's instruction. The site-directed mutagenesis primers were sense primer N62A For (5' ACT ATT GTT AAC ATT TTG ACT GCT AGA TCT AAC GCT CAA AGA CAA 3' (SEQ ID NO:9)) and antisense primer N62A Rev (5' TTG TCT TTG AGC GTT AGA TCT AGC AGT CAA AAT GTT AAC AAT AGT 3' (SEQ ID NO:10)). The mutated DNA construct was confirmed by sequencing; the full sequence is shown below (nts 1-1017 is A2; 1018-1025 code for the 6-His tag).

*P. Pastoris* Codon-Optimized DNA Sequence

Coding for Non-N-glycosylated Human Annexin A2-6×His

SEQ ID NO: 2

```
atgtctactgttcacgagattttgtgtaagttgtctttggagggtgaccactctactcca ccatctgcttacggttctgttaaggcttacactaacttcgacgctgagagagacgctttg aacattgagactgctattaagactaagggtgttgacgaggttactattgttaacattttg actGCTagatctaacgctcaaagacaagacattgctttcgcttaccaaagaagaactaag aaggagttggcttctgctttgaagtctgctttgtctggtcacttggagactgttattttg ggtttgttgaagactccagctcaatacgacgcttctgagttgaaggcttctatgaagggt ttgggtactgacgaggactctttgattgagattatctgttctagaactaaccaagagttg
```

```
-continued
caagagattaacagagtttacaaggagatgtacaagactgacttggagaaggacattatc tctgacacttctggtgacttcagaaagttgatggttgctttggctaagggtagaagagct gaggacggttctgttattgactacgagttgattgaccaagacgctagagacttgtacgac gctggtgttaagagaaagggtactgacgttccaaagtggatttctattatgactgagaga tctgttccacacttgcaaaaggttttcgacagatacaagtcttactctccatacgacatg ttggagtctattagaaaggaggttaagggtgacttggagaacgctttcttgaacttggtt caatgtattcaaaacaagccattgtacttcgctgacagattgtacgactctatgaagggt aagggtactagagacaaggttttgattagaattatggtttctagatctgaggttgacatg ttgaagattagatctgagttcaagagaaagtacggtaagtctttgtactactacattcaa caagacactaagggtgactaccaaaaggctttgttgtacttgtgtggtggtgacgaccac caccaccaccaccac
```

Example 2

*Pichia pastoris* Expression and Purification of the Glycosylated and Non-N-glycosylated Human Annexin A2

The glycosylated and non-N-glycosylated forms of human annexin A2 carrying 6×His-tag in the C-terminus were expressed as follows.

5-10 µg of the above constructed plasmid DNA was linearized by SacI digestion for 3 h at 37° C., treated with Qiagen PCR purification kit, and transformed into *Pichia pastoris* strain X33 using the Gene Pulser MXcell Electroporation system (Bio-Rad). Cells were spread on YPD agar plates (1% Bacto™ yeast extract, 2% Bacto™ peptone, 1.5% Bacto™ agar, 2% dextrose) containing 100 µg/ml of Zeocin and incubated at 30° C. for 3-4 days. Six colonies were randomly picked and cultivated in small tubes containing 5 mL YPD (1% Bacto™ yeast extract, 2% Bacto™ peptone, 2% dextrose) at 30° C. at 250 rpm for 24 h as growth phase I, then in YPG (1% Bacto™ yeast extract, 2% Bacto™ peptone, 1% glycerol) at 30° C. at 250 rpm for another 24 h as growth phase II. The cultures were induced in 2 mL BMMYC (1% Bacto™ yeast extract, 2% Bacto™ peptone, 100 mM potassium phosphate, pH 7.0, 1.34% yeast nitrogen base without amino acids (MP), $4 \times 10^{-5}$% biotin, 0.5% methanol and 1% Bacto™ casamino acids) for 48 h at 25° C. at 225 rpm. 0.5% methanol was added in the beginning and end of the day to sustain the methanol level. Antifoam 0.02% (Emerald Performance Materials, Cat# KF0673) was added in all of the growth and induction medium. 1 mM PMSF (Phenylmethanesulfonyl fluoride, Sigma) was added with methanol to inhibit the protein degradation during the induction phase. The culture supernatants were analyzed using 4-12% NuPAGE SDS gel under non-reducing conditions.

One clone for each of the glycosylated and non-N-glycosylated forms was selected and cultivated in shake-flasks (scaled up from the above described small tube expression) for downstream purification. 100 units/ml of penicillin and 100 µg/ml of streptomycin were added to suppress bacterial contamination. The supernatant was clarified by centrifugation at 3000 rpm at 4° C. for 10 minutes prior to protein purification.

Protein purification was performed as follows. Ni-Sepharose™ 6 Fast Flow was packed in a 5 cm×20 cm XK50 column (GE healthcare Cat#18-1000-71) for the first step purification. The column was equilibrated with 10 column volumes (CV) of 20 mM sodium phosphate pH 7.4, 0.5 M NaCl, and 5 mM imidazole. The sample was prepared by adding 0.5 M NaCl, 20 mM sodium phosphate pH 7.4, and 5 mM imidazole and filtered through crepe fluted filter paper (VWR) and loaded onto the equilibrated column. The column was washed using 20 mM sodium phosphate pH 7.4, 0.5 M NaCl, and 5 mM imidazole (6 or 8 CV). The bound proteins were eluted with 20 mM sodium phosphate pH 7.4, 0.5 M NaCl, 500 mM imidazole into eight fractions. The purification fractions were analyzed using 4-12% NuPAGE® Bis-Tris gel and stained with GelCode Blue stain reagent (Thermo Scientific). The fractions containing the protein of interest were pooled (FIGS. 2A and 3A, Elution fraction #2 to #4, 50 mL per fraction) and dialyzed using a 3.5 kDa cut off Spectra/Por® membrane tubing (Spectrumlabs) against 20 mM Tris-HCl pH 8.0, 1 mM EDTA pH 8.0, 5% glycerol at 4° C. The dialysis buffer was replaced once.

Strong cation exchange resin Poros® 50 HS (Applied Biosystems) in a XK16/20 column (GE Healthcare) was used for the second step purification. The column was equilibrated with 20 mM Tris-HCl pH 8.0, 1 mM EDTA, 5% glycerol (8 or 10 CV). The above dialyzed sample was loaded onto the column followed by washing with 20 mM Tris-HCl pH 8.0, 1 mM EDTA, 5% glycerol (8 CV). The bound protein was eluted with 50 and then 100 mM sodium borate (for the glycosylated version), or 100 and then 200 mM sodium borate (for the non-N-glycosylated version) in 20 mM Tris-HCl pH 8.0, 1 mM EDTA, 5% glycerol into eight fractions, respectively. The purified fractions were analyzed using 4-12% NuPAGE SDS gel. For the glycosylated version all of the elution fractions were pooled with 25, 50 and 100 mM sodium borate as final product. For non-N-glycosylated version the pooled flow-through and washing fractions were collected as group#1, and the 100 mM sodium borate elution fractions #2-8 were pooled as group #2. Since the group#1 was fully functional, this group was further purified using Ni-Sepharose 6 fast flow resin in a XK16/20 column (GE Healthcare) as described for the first step purification. The pooled protein product was concentrated down with Centricon Plus-70 (10 kDa cut off, Millipore), dialyzed against PBS pH 7.4+5% glycerol, filter sterilized and stored at 80° C. Protein concentration was determined using Pierce BCA protein assay kit (Thermo Scientific).

Western blotting analysis was performed as follows. Protein samples were separated by electrophoresis using NuPAGE 4-12% Bis-Tris Gel and the gel was electro-transferred at 35 V onto a nitrocellulose membrane filter paper using 1× NuPAGE® transfer buffer (Invitrogen). The membrane was thereafter blocked in 2% blotting grade blocker non-fat dry milk (Bio-Rad) in 1×PBS, 0.02% Tween 20 for 1 h with shaking and washed once with 1×PBS, pH7.4, 0.02% Tween 20 at room temperature with shaking. The glycosylated or non-N-glycosylated human annexin A2 were detected with mouse anti-His monoclonal antibody (1:500) (Invitrogen) and rat anti-mouse IgG-HRP (1:1000) (Invitrogen) in 5% non-fat dry milk in 1×PBS, 0.02% Tween 20. Detection of the proteins was done by TMB membrane peroxidase substrate (KPL Cat#: 50-77-02), and color development was stopped with $dH_2O$. The results demonstrated expression at a level of approximately ~140 mg/L.

The secreted glycosylated or non-N-glycosylated human annexin A2 was captured directly by Ni-Sepharose 6 fast flow resin through its 6×His-tag in the C-terminus mainly in the $2^{nd}$ and $3^{rd}$ fractions eluted (FIGS. 2A and 3A). The eluted fractions from the capturing step were pooled, concentrated down with Centricon Plus-70 (10 kDa cut off) and dialyzed to remove the salts for the second step purification. Based on the isoelectric point value (8.86) strong cation exchange resin POROS 50 HS (50 um strong cation exchange resin, Life Technologies) was chosen for the second step purification. In the second step purification sodium borate was applied to separate the glycosylated or non-N-glycosylated human annexin A2 from the glycosylated yeast host protein and aggregates (Woo et al., 2003). As shown in FIGS. 2B and 3B and FIG. 4, pure glycosylated or non-N-glycosylated human annexin A2 was obtained after a two-step purification. As shown in FIG. 3B, two group products were separately collected for non-N-glycosylated human annexin A2 because the SDS gel pattern differed between the two groups. As noted above, group #1 was the pooled flow-through and washing fractions. Group #2 was the pooled 100 mM sodium borate elution fractions (#2 to #8). Group #1 was further purified using Ni-Sepharose 6 fast flow resin (FIG. 3C) as this group was fully functional (see Example 3). As shown in FIGS. 2B and 3C both pure glycosylated and non-N-glycosylated human annexin A2 were obtained. The final product yield was ~50 mg/L for glycosylated human annexin A2 and ~40 mg/L from group #1 of the non-N-glycosylated human annexin A2.

Example 3

Amplifying Function Analysis for tPA-mediated Plasmin-generation by *Pichia pastoris* Expressed Glycosylated and Non-N-glycosylated Human Annexin A2

Glycosylated and non-glycosylated human annexin A2 were expressed in the *Pichia pastoris* system as described above. The plasmin activity was measured as described by Zhu et al., 2010. Briefly, the indicated individual or combined concentrations of the glycosylated or non-N-glycosylated human annexin A2 (labeled as rA2), tPA were added directly to wells of 96-well culture plate preloaded with N-terminal lysine plasminogen (2.5 mg/mL) and a fluorogenic plasmin substrate, D-Val-Leu-Lys-AMC (200 nmol/L) in a final volume of 100 μL PBS. After incubation at 37° C. for 30 mins, plasmin generation or activity was read on a fluorescent plate reader at excitation 360 nm and emission 460 nm (Ishii et al, 2001).

As shown in FIG. 5, glycosylated human annexin A2 expressed in *Pichia pastoris* did not significantly enhance tPA-mediated plasmin-generation (labeled as t1+y-N-gly-rA2), when compared to the negative control (labeled as control), which indicated that the enhancer function for tPA-mediated plasmin-generation was almost completely lost. It was hypothesized that the *Pichia pastoris* high-mannose N-linked glycosylation could be the cause of the loss of this enhancer function. Thus, the unique N-glycosylation site in the human annexin A2 gene was mutated as described above. *Pichia pastoris*-expressed non-N-glycosylated human annexin A2 group #1 restored the enhancer function completely (FIG. 5, labeled as t1+y-rA2 group #1) comparable to the *E. coli* expressed human annexin A2 (positive control, labeled as t1+bac-rA2). The enhancer function was partially (about 50%) restored in group #2 (FIG. 5, labeled as t1+y-rA2 group #2). Group #1 and group #2 were separated by the second step purification (see Example 2 above). These results demonstrated that the high-mannose N-linked glycosylation was a likely cause of the loss of enhancer function for tPA-mediated plasmin-generation. Why the biological function of group #2 was not completely recovered is presently unknown. The functional analysis also demonstrated that the 6×His tag added in the C-terminus did not influence the enhancer function for tPA-mediated plasmin-generation. This His-tag can be removed or omitted for pharmaceutical drug development and other methods, such as hydrophobic chromatography, can be used to directly capture the secreted non-N-glycosylated human annexin A2.

These results also demonstrated that the codon-optimization strategy described herein is ideal for the *Pichia pastoris* expression system to express the human annexin A2. Since the dose requirement for the enhancer function in vivo is very high (5 mg/kg, Zhu et al 2010), cost-effectiveness, high production level, high purity, easy purification is needed. As presented in this study, the *Pichia pastoris* expressed non-N-glycosylated human annexin A2 met all of the above requirements.

REFERENCES

Cohen J E, Itshayek E, Moskovici S, Gomori J M, Fraifeld S, Eichel R, Leker R R. (2011) State-of-the-art reperfusion strategies for acute ischemic stroke, J Clin Neurosci. 18:319-323.

Davalos A. (2005) Thrombolysis in acute ischemic stroke: successes, failures, and new hopes. Cerebrovasc Dis. 20 (Suppl 2):135-139

Ishii H, Yoshida M, Hiraoka M, Hajjar K A, Tanaka A, Yasukochi Y, Numano F. (2001) Recombinant annexin II modulates impaired fibrinolytic activity in vitro and in rat carotid artery. Circ Res. 89:1240-1245.

Hajjar K A, Menell J S. (1997) Annexin II: a novel mediator of cell surface plasmin generation. Ann NY Acad Sci. 811: 337-349.

Kaur J, Zhao Z, Klein G M, Lo E H, Buchan A M. (2004) The neurotoxicity of tissue plasminogen activator. J Cereb Blood Flow Metab. 24:945-963.

Kim J, Hajjar K A. (2002) Annexin II: a plasminogen-plasminogen activator co-receptor. Front Biosci. 7:d341-d348.

Sreekrishna K, Strategies for optimizing protein expression and secretion in the methylotrophic yeast *Pichia pastoris*, in: R. H. Baltz, G. D. Hegeman, P. L. Skatrud (Eds.), Industrial Microorganism: Basic and Applied Molecular Genetics, Am. Soc. Microbiol., Washington, D.C., 1993, pp. 119-126.

Walvick R P, Bråtane B T, Henninger N, Sicard K M, Bouley J, Yu Z, Lo E, Wang X, Fisher M. (2011) Visualization of clot lysis in a rat embolic stroke model: application to comparative lytic efficacy. Stroke 42:1110-1115.

Wang X, Tsuji K, Lee S R, Ning M, Furie K L, Buchan A M, Lo E H. (2004) Mechanisms of hemorrhagic transformation after tissue plasminogen activator reperfusion therapy for ischemic stroke. Stroke 35:2726-2730

Woo J H, Liu Y Y, Mathias A, Stavrou S, Wang Z, Thompson J, Neville DM Jr. (2002) Gene optimization is necessary to express a bivalent anti-human anti-T cell immunotoxin in *Pichia pastoris*. Protein Expr Purif. 25:270-282.

Woo J H, Neville D M Jr. (2003) Separation of bivalent anti-T cell immunotoxin from *Pichia pastoris* glycoproteins by borate anion exchange. Biotechniques 35:392-398.

Yepes M, Roussel B D, Ali C, Vivien D. (2009) Tissue-type plasminogen activator in the ischemic brain: more than a thrombolytic. Trends Neurosci. 32:48-55.

Zhu H, Fan X, Yu Z, Liu J, Murata Y, Lu J, Zhao S, Hajjar K A, Lo E H, Wang X. (2010) Annexin A2 combined with low-dose tPA improves thrombolytic therapy in a rat model of focal embolic stroke. J Cereb Blood Flow Metab, 30:1137-1146.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A non-N-glycosylated human annexin A2 comprising SEQ ID NO:1, wherein the amino acid at position 62 is alanine (A) or glycine (G); and/or the amino acid at position 64 is neither Threonine (T) nor Serine (S).

2. The non-N-glycosylated human annexin A2 of claim 1, wherein the amino acid at position 62 is Alanine (A) or Glycine (G).

3. A codon-optimized nucleic acid molecule encoding the non-N-glycosylated human annexin A2 of claim 1.

4. A vector comprising the nucleic acid molecule of claim 3.

5. A non-human host cell expressing the nucleic acid molecule of claim 3.

6. The host cell of claim 5, wherein the host cell is a methylotropic yeast.

7. The host cell of claim 6, wherein the host cell is a cell of the species *Pichia Pastoris*.

8. A pharmaceutical composition comprising the non-N-glycosylated human annexin A2 of claim 1 and a physiologically acceptable carrier.

9. The pharmaceutical composition of claim 8, further comprising an additional active agent.

10. A method of treating a subject who has a vascular disorder associated with thrombus formation, the method comprising administering to the subject a therapeutically effective amount of the non-N-glycosylated human annexin A2 comprising SEQ ID NO: 1, wherein the amino acid at position 62 is alanine (A) or glycine (G); and/or the amino acid at position 64 is neither Threonine (T) nor Serine (S).

11. The method of claim 10, wherein the vascular disorder associated with thrombus formation is selected from the group consisting of ischemic stroke, cerebral venous thrombosis (CVT), myocardial infarction (MI), deep vein thrombosis (DVT), pulmonary embolism (PE), peripheral arterial disease (PAD), and blocked catheters.

12. A method of producing a composition comprising a non-N-glycosylated human annexin A2, the method comprising:
expressing a non-N-glycosylated human annexin A2 comprising SEQ ID NO: 1, wherein the amino acid at position 62 is alanine (A) or glycine (G); and/or the amino acid at position 64 is neither Threonine (T) nor Serine (S), in a methylotropic yeast; and
substantially purifying the non-N-glycosylated human annexin A2, thereby producing the composition.

13. The method of claim 12, wherein substantially purifying the non-N-glycosylated human annexin A2 comprises: contacting a composition comprising non-N-glycosylated human annexin A2 with a strong cation exchange resin; and collecting fractions having higher annexin 2 biological activity.

14. The method of claim 13, comprising collecting one or both of a flow-through and a washing fraction.

15. A heterologous protein expression system host cell expressing the nucleic acid molecule of claim 3.

* * * * *

UNITED STATES PATENT AND TRADEMARK OFFICE
CERTIFICATE OF CORRECTION

PATENT NO.       : 9,314,500 B2
APPLICATION NO.  : 14/351008
DATED            : April 19, 2016
INVENTOR(S)      : Zhirui Wang Page 1 of 1

It is certified that error appears in the above-identified patent and that said Letters Patent is hereby corrected as shown below:

Claims

In column 27, line 49, in Claim 6, delete "methylotropic" and insert -- methylotrophic --;

In column 28, line 48 (approx.), in Claim 12, delete "methylotropic" and insert -- methylotrophic --;

In column 28, line 50 (approx.), in Claim 12, delete "A2,thereby" and insert -- A2, thereby --.

Signed and Sealed this
Twelfth Day of July, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 339
<212> TYPE: PRT
<213> ORGANISM: Artificial Sequence
<220> FEATURE:
<223> OTHER INFORMATION: human Annexin 2 with two potential mutation
      sites
<220> FEATURE:
<221> NAME/KEY: VARIANT
<222> LOCATION: 62
<223> OTHER INFORMATION: Xaa = any amino acid other than asparagine (N)
<220> FEATURE:
<221> NAME/KEY: VARIANT
<222> LOCATION: 64
<223> OTHER INFORMATION: Xaa = any amino acid other than serine (S) or
      threonine (T)

<400> SEQUENCE: 1

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Xaa Arg Xaa
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205
```

```
Asp Val Pro Lys Trp Ile Ser Ile Met Thr Glu Arg Ser Val Pro His
    210                 215                 220
Leu Gln Lys Val Phe Asp Arg Tyr Lys Ser Tyr Ser Pro Tyr Asp Met
225                 230                 235                 240
Leu Glu Ser Ile Arg Lys Glu Val Lys Gly Asp Leu Glu Asn Ala Phe
                    245                 250                 255
Leu Asn Leu Val Gln Cys Ile Gln Asn Lys Pro Leu Tyr Phe Ala Asp
                260                 265                 270
Arg Leu Tyr Asp Ser Met Lys Gly Lys Gly Thr Arg Asp Lys Val Leu
                275                 280                 285
Ile Arg Ile Met Val Ser Arg Ser Glu Val Asp Met Leu Lys Ile Arg
        290                 295                 300
Ser Glu Phe Lys Arg Lys Tyr Gly Lys Ser Leu Tyr Tyr Tyr Ile Gln
305                 310                 315                 320
Gln Asp Thr Lys Gly Asp Tyr Gln Lys Ala Leu Leu Tyr Leu Cys Gly
                    325                 330                 335
Gly Asp Asp
```

<210> SEQ ID NO 2
<211> LENGTH: 1035
<212> TYPE: DNA
<213> ORGANISM: Artificial Sequence
<220> FEATURE:
<223> OTHER INFORMATION: DNA encoding human annexin A2-6xHis with N62A
      mutation, Codon-optimized for Pichia pastoris
      expression

<400> SEQUENCE: 2

```
atgtctactg ttcacgagat tttgtgtaag ttgtctttgg agggtgacca ctctactcca      60
ccatctgctt acggttctgt taaggcttac actaacttcg acgctgagag agacgctttg     120
aacattgaga ctgctattaa gactaagggt gttgacgagg ttactattgt taacattttg     180
actgctagat ctaacgctca agacaagac attgctttcg cttaccaaag aagaactaag     240
aaggagttgg cttctgcttt gaagtctgct ttgtctggtc acttggagac tgttattttg     300
ggtttgttga agactccagc tcaatacgac gcttctgagt tgaaggcttc tatgaagggt     360
ttgggtactg acgaggactc ttttgattga gattatctgtt ctagaactaa ccaagagttg     420
caagagatta cagagttta caaggagatg tacaagactg acttggagaa ggacattatc     480
tctgacactt ctggtgactt cagaaagttg atggttgctt ggctaaggg tagaagagct     540
gaggacggtt ctgttattga ctacgagttg attgaccaag acgctagaga cttgtacgac     600
gctggtgtta agagaaaggg tactgacgtt ccaaagtgga tttctattat gactgagaga     660
tctgttccac acttgcaaaa ggttttcgac agatacaagt cttactctcc atacgacatg     720
ttggagtcta ttagaaagga ggttaagggt gacttggaga cgctttcttt gaacttggtt     780
caatgtattc aaaacaagcc attgtacttc gctgacagat tgtacgactc tatgaagggt     840
aagggtacta gagacaaggt tttgattaga attatggttt ctagatctga ggttgacatg     900
ttgaagatta gatctgagtt caagagaaag tacggtaagt cttttgtacta ctacattcaa     960
caagacacta agggtgacta ccaaaaggct ttgttgtact gtgtggtgg tgacgaccac    1020
caccaccacc accac                                                    1035
```

<210> SEQ ID NO 3
<211> LENGTH: 1035
<212> TYPE: DNA
<213> ORGANISM: Artificial Sequence
<220> FEATURE:
<223> OTHER INFORMATION: DNA encoding human annexin A2-6xHis
      Codon-optimized for Pichia pastoris expression

<400> SEQUENCE: 3

```
atgtctactg ttcacgagat tttgtgtaag ttgtctttgg agggtgacca ctctactcca      60
ccatctgctt acggttctgt taaggcttac actaacttcg acgctgagag agacgctttg     120
aacattgaga ctgctattaa gactaagggt gttgacgagg ttactattgt taacattttg     180
actaacagat ctaacgctca agacaagac attgctttcg cttaccaaag aagaactaag      240
aaggagttgg cttctgcttt gaagtctgct ttgtctggtc acttggagac tgttattttg     300
ggtttgttga agactccagc tcaatacgac gcttctgagt tgaaggcttc tatgaagggt     360
ttgggtactg acgaggactc tttgattgag attatctgtt ctagaactaa ccaagagttg     420
caagagatta acagagttta caaggagatg tacaagactg acttggagaa ggacattatc     480
tctgacactt ctggtgactt cagaaagttg atggttgctt ggctaaaggg tagaagagct     540
gaggacggtt ctgttattga ctacgagttg attgaccaag acgctagaga cttgtacgac     600
gctggtgtta agagaaaggg tactgacgtt ccaaagtgga tttctattat gactgagaga     660
tctgttccac acttgcaaaa ggttttcgac agatacaagt cttactctcc atacgacatg     720
ttggagtcta ttagaaagga ggttaagggt gacttggaga acgctttctt gaacttggtt     780
caatgtattc aaaacaagcc attgtacttc gctgacagat gtacgactc tatgaagggt      840
aagggtacta gagacaaggt tttgattaga attatggttt ctagatctga ggttgacatg     900
ttgaagatta gatctgagtt caagagaaag tacggtaagt cttgtacta ctacattcaa      960
caagacacta agggtgacta ccaaaaggct ttgttgtact gtgtggtgg tgacgaccac     1020
caccaccacc accac                                                     1035
```

<210> SEQ ID NO 4
<211> LENGTH: 345
<212> TYPE: PRT
<213> ORGANISM: Artificial Sequence
<220> FEATURE:
<223> OTHER INFORMATION: human annexin A2 with 6His tag

<400> SEQUENCE: 4

```
Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140
```

```
Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
                180                 185                 190

Gln Asp Ala Arg Asp Leu Tyr Asp Ala Gly Val Lys Arg Lys Gly Thr
                195                 200                 205

Asp Val Pro Lys Trp Ile Ser Ile Met Thr Glu Arg Ser Val Pro His
                210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
                260                 265                 270

Arg Leu Tyr Asp Ser Met Lys Gly Lys Gly Thr Arg Asp Lys Val Leu
                275                 280                 285

Ile Arg Ile Met Val Ser Arg Ser Glu Val Asp Met Leu Lys Ile Arg
                290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp His His His His His
                340                 345

<210> SEQ ID NO 5
<211> LENGTH: 8
<212> TYPE: PRT
<213> ORGANISM: Artificial Sequence
<220> FEATURE:
<223> OTHER INFORMATION: FLAG tag peptide

<400> SEQUENCE: 5

Asp Tyr Lys Asp Asp Asp Asp Lys
1               5

<210> SEQ ID NO 6
<211> LENGTH: 6
<212> TYPE: PRT
<213> ORGANISM: Artificial Sequence
<220> FEATURE:
<223> OTHER INFORMATION: haemagglutinin tag peptide

<400> SEQUENCE: 6

Tyr Pro Tyr Asp Val Pro
1               5

<210> SEQ ID NO 7
<211> LENGTH: 10
<212> TYPE: PRT
<213> ORGANISM: Artificial Sequence
<220> FEATURE:
<223> OTHER INFORMATION: myc tag peptide

<400> SEQUENCE: 7

Ile Leu Lys Lys Ala Thr Ala Tyr Ile Leu
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: myc tag peptide

<400> SEQUENCE: 8

Glu Gln Lys Leu Ile Ser Glu Glu Asp Leu
1               5                   10

<210> SEQ ID NO 9
<211> LENGTH: 45
<212> TYPE: DNA
<213> ORGANISM: Artificial Sequence
<220> FEATURE:
<223> OTHER INFORMATION: PCR primer N62A For

<400> SEQUENCE: 9
actattgtta acattttgac tgctagatct aacgctcaaa gacaa              45

<210> SEQ ID NO 10
<211> LENGTH: 45
<212> TYPE: DNA
<213> ORGANISM: Artificial Sequence
<220> FEATURE:
<223> OTHER INFORMATION: PCR antisense primer N62A Rev

<400> SEQUENCE: 10
ttgtctttga gcgttagatc tagcagtcaa aatgttaaca atagt              45
```